United States Patent
Lee et al.

(10) Patent No.: US 9,378,334 B2
(45) Date of Patent: Jun. 28, 2016

(54) MEDICAL PUMP PROVIDING CUSTOMIZABLE PROGRAMMING PERMISSIONS

(75) Inventors: Chaoyoung Lee, Weston, MA (US); Mei Zhang, Sharon, MA (US)

(73) Assignee: Zyno Medical, LLC, Natick, MA (US)

(*) Notice: Subject to any disclaimer, the term of this patent is extended or adjusted under 35 U.S.C. 154(b) by 359 days.

(21) Appl. No.: 13/489,620

(22) Filed: Jun. 6, 2012

(65) Prior Publication Data

US 2012/0310205 A1 Dec. 6, 2012

Related U.S. Application Data

(60) Provisional application No. 61/589,204, filed on Jan. 20, 2012, provisional application No. 61/493,680, filed on Jun. 6, 2011.

(51) Int. Cl.
*A61M 5/168* (2006.01)
*G06F 19/00* (2011.01)
(Continued)

(52) U.S. Cl.
CPC ........ *G06F 19/3412* (2013.01); *G06F 19/3418* (2013.01); *A61M 5/1456* (2013.01); *A61M 5/14228* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/52* (2013.01);
(Continued)

(58) Field of Classification Search
CPC ............ G06F 19/3468; G06F 19/3412; G06F 19/3418; G06F 19/3456; G06F 19/3406; G06F 19/326; A61M 2205/3553; A61M 2205/3584; A61M 2205/3592; A61M 2205/50; A61M 2205/502; A61M 2205/52; A61M 2205/6009; A61M 2205/6018; A61M 2205/6054; A61M 2205/6072; A61M 5/14228; A61M 5/1456; A61M 5/172
USPC ........... 604/151, 66, 67, 131, 65, 30, 31, 500, 604/503; 38/151, 66, 67, 131, 65, 30, 31, 38/500, 503
See application file for complete search history.

(56) References Cited

U.S. PATENT DOCUMENTS 4,475,901 A * 10/1984 Kraegen et al. ................. 604/67
5,069,668 A * 12/1991 Boydman ..................... 604/121
(Continued)

FOREIGN PATENT DOCUMENTS

| CN | 1748219 A | 3/2006 |
|---|---|---|
| CN | 1784684 A | 6/2006 |
| EP | 0871505 B1 | 10/1998 |

OTHER PUBLICATIONS

Chinese Search Report issued by SIPO on Apr. 28, 2014; Patent App No. 2012101835752.
(Continued)

*Primary Examiner* — Kevin C Sirmons
*Assistant Examiner* — William Carpenter
(74) *Attorney, Agent, or Firm* — Boyle Fredrickson, S.C.

(57) ABSTRACT

A method and apparatus for delivering intravenous drugs to a patient provides for remote loading and programming of IV pumps that may be shipped in a loaded and programmed configuration to a remote site for use with the patient. A special carrier may be provided for pneumatic delivery of the preloaded pump. Password enabled customizing of pump features according to specific user's need may be provided to prevent undesired changing of the pump parameters at the remote site.

19 Claims, 5 Drawing Sheets

(51) Int. Cl.
*A61M 5/142* (2006.01)
*A61M 5/145* (2006.01)

(52) U.S. Cl.
CPC .............. *A61M 2205/6009* (2013.01); *A61M 2205/6018* (2013.01); *A61M 2205/6054* (2013.01); *A61M 2205/6072* (2013.01)

(56) References Cited

U.S. PATENT DOCUMENTS

| | | | |
|---|---|---|---|
| 5,181,910 A | 1/1993 | Scanlon | |
| 5,562,615 A * | 10/1996 | Nassif | A61M 5/16831 128/DIG. 13 |
| 5,755,563 A * | 5/1998 | Clegg et al. | 417/326 |
| 5,895,371 A | 4/1999 | Levitas et al. | |
| 5,935,099 A * | 8/1999 | Peterson | A61M 5/172 604/65 |
| 6,671,563 B1 | 12/2003 | Engelson et al. | |
| 6,731,989 B2 | 5/2004 | Engleson et al. | |
| 6,745,764 B2 * | 6/2004 | Hickle | 128/203.12 |
| 6,790,198 B1 * | 9/2004 | White | A61M 5/142 604/151 |
| 7,347,836 B2 * | 3/2008 | Peterson | A61M 5/14228 604/31 |
| 7,933,780 B2 | 4/2011 | De La Huerga | |
| 8,444,592 B2 * | 5/2013 | Williams et al. | 604/27 |
| 2001/0021817 A1 * | 9/2001 | Brugger | A61M 1/3626 604/6.11 |
| 2002/0058906 A1 * | 5/2002 | Lebel et al. | 604/65 |
| 2002/0107476 A1 * | 8/2002 | Mann et al. | 604/67 |
| 2004/0193453 A1 | 9/2004 | Butterfield et al. | |
| 2005/0177395 A1 | 8/2005 | Blomquist | |
| 2006/0079767 A1 * | 4/2006 | Gibbs et al. | 600/432 |
| 2006/0173444 A1 * | 8/2006 | Choy et al. | 604/891.1 |
| 2007/0167912 A1 * | 7/2007 | Causey | A61M 5/14244 604/131 |
| 2008/0065007 A1 | 3/2008 | Peterson et al. | |
| 2008/0161753 A1 | 7/2008 | Gillespie et al. | |
| 2009/0069785 A1 * | 3/2009 | Miller et al. | 604/500 |
| 2010/0280486 A1 * | 11/2010 | Khair | A61M 5/142 604/506 |

OTHER PUBLICATIONS

Supplemental Chinese Search Report issued by SIPO on Dec. 31, 2014; Patent App No. 201210183575.2.

* cited by examiner

MEDICAL PUMP PROVIDING CUSTOMIZABLE PROGRAMMING PERMISSIONS

CROSS-REFERENCE TO RELATED APPLICATION

This application claims the benefit of U.S. Provisional Application No. 61/589,204 filed Jan. 20, 2012 and entitled System for Remote Programming and Loading of Medical Pumps; and further claims the benefit of U.S. Provisional Application No. 61/493,680 filed Jun. 6, 2011, entitled: Concepts of Customizing Infusion Pumps and further claims the benefit of hereby incorporated by reference.

BACKGROUND OF THE INVENTION

The present invention relates to medical pumps for the delivery of medicines to patients under controlled rates and dosages and in particular to a pump adapted for remote loading and set up.

Medical pumps, such as syringe pumps or peristaltic infusion pumps, are known for computer-controlled delivery of medication or contrast agents (henceforth drugs) to patients over a period of time. Typically the drug is delivered in a syringe (for a syringe pump) or a flexible bag (for peristaltic infusion pump) that may be connected to an IV line attached to a needle for insertion into the patient. When a nurse or other healthcare professional ministering to the patient receives the drug, the healthcare professional reviews the drug description for correctness and enters the desired dose and rate into the pump. The syringe or IV line must then be mechanically connected to the pump mechanism and the mechanism activated to begin pumping.

The process of programming pumps and mechanically attaching the drug container (syringes or bags and IV lines) to the pump mechanism can be time-consuming and exacting. In a large facility, there may be multiple different pump designs and models and a given healthcare professional ministering to a patient may be called upon only occasionally to work with any given type of pump. This variation in pump types can increase the time required to properly initialize and connect the pump mechanism, and create errors in dose programming or mechanical installation that can carry with them significant risks to the patient and/or cause waste of the necessary drug. Failure to properly set up or connect the drug container to the pump can raise safety issues.

The difficulties of setting up and programming pumps can also be a problem when the pumps are used in a home setting. In such cases, normally a nurse will deliver and attend to the proper initialization of the pump.

SUMMARY OF THE INVENTION

The present invention provides a method and apparatus for improving the workflow of drug delivery to patients using medical pumps, in which the pump may be programmed and loaded remotely by a specialist such as a pharmacist and then shipped in connected form to the healthcare professional ministering to the patient. This healthcare professional then needs only install the pump and pre-loaded drug container on a pole or the like and ensure connection to the patient (possibly through an existing IV line) to begin pumping operation. The simplified workflow significantly mitigates the risks of improper programming of the infusion pumps or improper loading of IV set. The pump may require verification of the setup (proper drug and patient) significantly reducing any risks of such a remote loading operation. In addition, programming features may be hidden, limited and locked by the specialist.

One embodiment of the present invention provides a method of managing patient drug infusions in which a drug infusion order is received by a first individual, at a first work area, the order providing a drug identification and infusion parameters. The first individual loads a medical pump with a drug container as attached to an IV line per the drug identification and programs the medical pump with the infusion parameters. The loaded and programmed medical pump is then transferred to a second individual at a second work area remote from the first work area. The second individual connects the IV line to the patient and activates the medical pump according to its previous programming by the first individual and using the drug container loaded by the first individual. Depending on the practical need(s), the first individual may only program the pump or only load the pump with tubing/container.

It is thus a feature of at least one embodiment of the invention to allow the specialized knowledge of pump programming and loading to be centralized with an individual to better leverage the skill of that individual. It is a further feature of at least one embodiment of the invention to better manage the complexity of loading and programming of multiple different types of pumps.

The method may include the step of requiring validation by the second individual at the second work area of certain infusion parameters before activation of the medical pump.

It is thus a feature of at least one embodiment of the invention to permit remote loading and programming of medical pumps while ensuring proper validation of the setup and operation of the pumps at a remote location when the programming and drug installation has been previously performed. Requiring the second individual to validate selective parameters provides a check against transportation errors and the like.

The infusion parameters may include patient identification, drug identification, and drug delivery rate.

It is thus a feature of at least one embodiment of the invention to provide for validation both of patient and/or fundamental delivery parameters.

The medical pump may be an infusion pump and the drug may be contained in an IV bag attached to an IV line and the loading of the medical pump with the drug may include the steps of threading the IV line through the pump and locking the tubing into the pump.

It is thus a feature of at least one embodiment of the invention to centralize the installation of an IV line into multiple elements of a pump.

The method may include the step of loading the pump into a carrier configured to hold the pump and drug during the transportation.

It is thus a feature of at least one embodiment of the invention to provide a mechanism for transporting a loaded infusion pump that could otherwise be susceptible to dislodgment of the drug container and/or IV tube or damage to the same. It is thus a feature of at least one embodiment of the invention to permit the efficiencies of centralized drug dispensing and pump loading to be realized in a hospital environment.

The pump may provide a password locking of the programming and include the step of locking the programming of the pump.

It is thus a feature of at least one embodiment of the invention to provide improved accountability for pump programming in a remote loading system.

The pump may provide a password locking of rules describing a relationship between values of the programming and constraining a reprogramming of the pump by the second individual at the second work area.

It is thus a feature of at least one embodiment of the invention to permit limited ability by the remote user to change parameters within predefined relationships and ranges.

The password may protect a setting providing selective display of infusion parameters.

It is thus a feature of at least one embodiment of the invention to hide unnecessary programming options from the remote user.

These particular features and advantages may apply to only some embodiments falling within the claims and thus do not define the scope of the invention.

DETAILED DESCRIPTION OF THE PREFERRED EMBODIMENT

Figure 1:
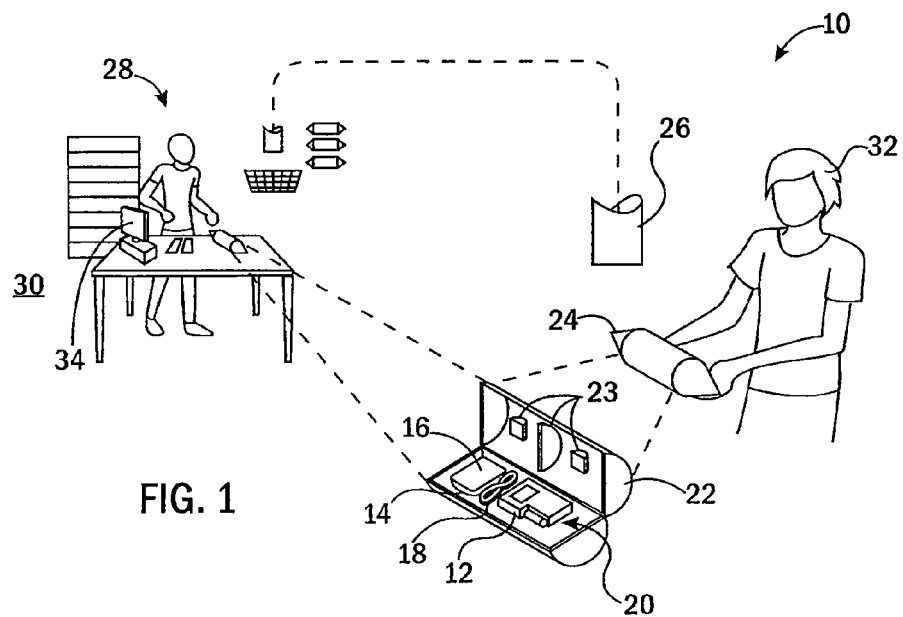
FIG. 1 is a simplified workflow diagram showing remote loading of a pump by a pharmacist and pneumatic transport of the loaded pump to a site of use in a pneumatic capsule as is possible with the present invention.

Referring now to FIG. 1, in an example workflow 10 that may be implemented by the present invention, a medical pump 12 (such as a syringe pump or a peristaltic pump) may be pre-loaded with the desired drug 14 (for example a medicine or contrast agent). In one embodiment, the drug 14 may be, for example, contained in a flexible pouch 16 communicating through tubing 18 to a connector 20 or sterile needle for attachment to a patient. Generally, the tubing 18 may be engaged within a pumping mechanism of the pump 12, the latter which may provide controlled flow of the drug to the patient as is understood in the art.

Each of the pump 12, pouch 16, tubing 18 and connector 20 may then be loaded into a carrier 22, for example, being part of a pneumatic cartridge 24 or a container fitting within a standard pneumatic cartridge 24 suitable for transportation over a hospital pneumatic system 26 for inter-hospital delivery. For this purpose, the pump 12, pouch 16, tubing 18 and connector 20 are sized to fit within the dimensions of a standard pneumatic cartridge 24 providing less than a 10 inch internal diameter (and preferably less than six inch diameter) and to have a weight of less than 20 pounds normally required for such systems and preferably less than 12 pounds.

As is understood in the art, pneumatic systems 26 may use air pressure to convey the pneumatic cartridge 24 holding the pump 12, pouch 16, tubing 18, and connector 20 as pre-assembled and programmed at speeds of up to 25 feet per second in the hospital or dispensing environment. Pneumatic cartridges 24 and pneumatic systems 26 suitable for this use are commercially available from Swisslog Healthcare Solutions of Buchs, Switzerland. An infusion pump suitable for this purpose and having the proper size and weight for pneumatic transport is commercially available from SIGMA International General Medical Apparatus, LLC of Medina, N.Y. (acquired by Baxter International Inc), although the present invention is not limited to this pump system.

Alternatively, the carrier 22 may be in the form of a suitcase for home delivery. In each case, the carrier 22 may include pads and dividers 23 for stabilizing its specialized contents against damage or disconnection. The preloading may be performed by a pharmacist 28 at a remote location 30, for example a central pharmacy and drug repository area within the hospital, and then loaded into the pneumatic system 26 for transportation to a nurse 32 or other healthcare professional administering to a patient.

Figure 2:
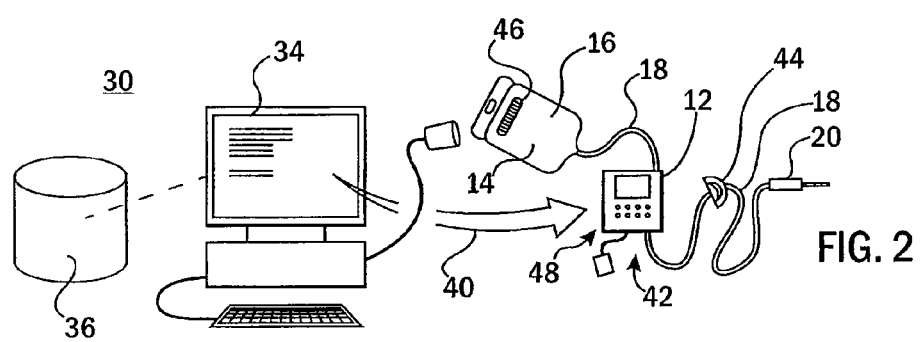
FIG. 2 is a data flow diagram showing communication between a computer of a pharmacist or other drug specialist and the pump for programming the pump after it has been loaded with the necessary drug by the pharmacist or drug specialist.
Figure 5:
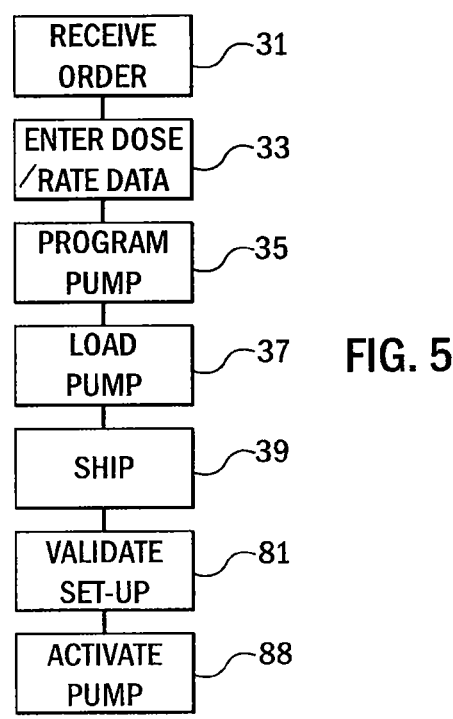
FIG. 5 is a flowchart of one embodiment of the workflow steps of the present invention implemented in part by electronic computer.

Referring now to FIGS. 1, 2 and 5, at the remote location 30, the pharmacist 28 may receive a drug order as indicated by process block 31 from a physician with necessary authentication by that physician and indicating a patient and a drug type. This order may be received electronically over an electronic medical record system 36 (FIG. 2) communicating with a terminal 34 (FIG. 2) accessible by the pharmacist 28 (FIG. 1). The pharmacist 28 may then determine the appropriate dose and rate (if not provided by the physician), for example, as may be based on information about the patient such as the patient's weight and other concurrently administered drugs and the like. Such information may also be obtained from a drug library. The pharmacist 28 may then enter this information into the terminal 34 for integration into the patient's record in the electronic medical record system 36 which may include review features, for example decision support tools detecting drug interactions or the like. This data entry is indicated by process block 33

The pharmacist 28 may then program the pump 12 to deliver the drug 14 at the correct dose and rate as indicated by process block 35 (FIG. 5). This programming may further provide the name of the patient and identify the drug 14 which may also be stored in the pump 12 as will be described. This programming by the pharmacist 28 may be simplified because of the frequent experience of the pharmacist 28 with the pump programming process. As will be discussed in greater detail below, the pharmacist 28 may lock certain programming features and may hide other programming features as part of this process.

A variety of methods may be used by the pharmacist 28 to program the pump 12 including manual programming of the pump using its keypad (as will be described below), wireless programming received by a wireless link in the pump 12 (either radio or infrared links), programming an RFID tag that may be installed on the pump 12 or close to the pump 12 (for example in the clamp 44 described below), or direct wired connection between a terminal 34 and the pump 12, for example a USB connection. The terminal 34 may be a standard desktop computer system providing for improved user interface capabilities, for example a full keyboard and large display. The terminal 34 may further include an interpreter allowing a standard user interface to be used with a variety of different pump types. Portable devices such as an iPhone, iPad, or other brand of tablet and mobile devices including cellphones, a desktop or laptop computer may be utilized to fulfill the function of terminal 34 by wired or wireless connection to the pump 12.

As indicated by process block 37, the pharmacist 28 may then install the drug into the pump 12, for example, by threading the tubing 18 through a pump section 42 of the pump 12 (FIG. 3), locking the tubing in place (for example by closing a door over the tubing), removing air from the tubing 18 to prime the tubing 18 and installing a clamp 44 (FIG. 2) on the tubing for shipment. The clamp may also be a built-in component on the IV set. The pharmacist may input drug and patient information on the clamp, for example, by utilizing an RFID that attaches to the clamp. In this case, an alternate work-flow is that the clamp carries all necessary information. Only the drug pouch and connected IV set are necessary to be transported from the pharmacy to the care site, where the pump is already mounted on the IV pole. Once the clamp is inserted into the pump, information can be read by the pump and processed. Again, the pharmacist 28, dealing with the pump on a regular basis, may have greater familiarity with tube loading and pump programming process than the nurse 32.

At this time the pharmacist 28 may record a barcode 46 on the pouch 16 and a barcode 48 on the pump 12 for recordkeeping purposes and/or to validate the proper drug has been installed. The barcode 48 enables proper monitoring of service of the pumps 12 which now move from location to location.

As was discussed above, the loaded and programmed pump 12 may then be installed in the carrier 22 for shipment as indicated by process block 39. While a pneumatic system 26 has been described, it will be appreciated that this shipment may be by a variety of different methods and may transport the loaded and programmed pump 12 out of the hospital environment for home use and the like. Further, the programming and loading may take place in other non-hospital environments, such as a pharmacy; it may be performed by a skill person who is not necessarily a pharmacist.

Figure 3:
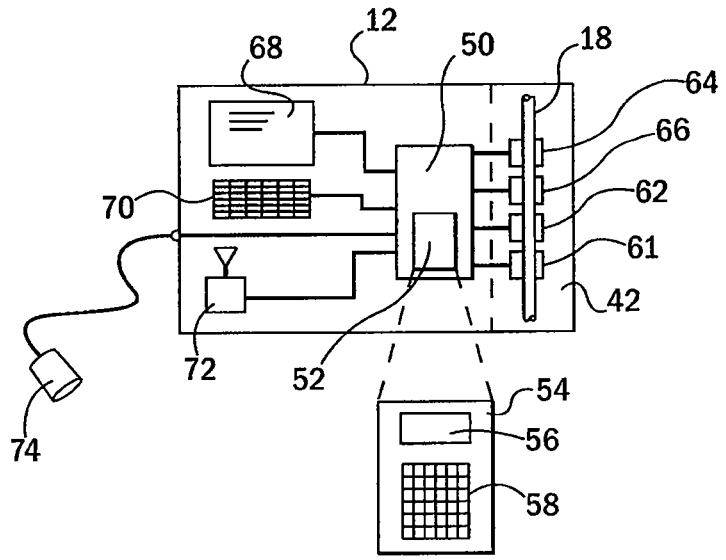
FIG. 3 is a block diagram of the principal elements of the pump including a user interface and controller holding a pump control program as well as control parameters providing information about the patient dose/rate and drug type for on-site verification.

Referring now to FIG. 3, the pump 12 may include a controller 50 (which may be a microprocessor based system) having a memory 52 for holding a stored operating program 54 including operating programs 56 controlling intrinsic operation of the pump 12. The memory 52 may also hold infusion parameter data 58 in a data table, the infusion parameter data 58 including identification of the patient, values for a dose and rate of desired drug delivery, alarm settings and the like, and a drug name. Each of the infusion parameter data 58 is programmable according to a programming method 40 (FIG. 2) as described above as well as other program modes which will be discussed in more detail below.

The controller 50 using the data in the memory 52 may control a pump section 42 of the pump 12 during delivery of drug 14 to the patient. The pump section 42 may, for example, include one or more pressure sensors 61 monitoring pressure in the IV tubing 18 installed in the pump section 42 or detecting blockage or other pumping irregularities. In addition, the pump section 42 may include a bubble sensor 62 for detecting bubbles in the IV tubing 18, a pump 64, for example, providing successive compressing elements for peristaltically moving fluid through the IV tubing 18, and the flow sensor 66 for detecting a flow rate of liquid in the IV tubing. Each of these sensors 61, 62, and 66 and the pump 64 may communicate with the controller 50 so that the pumping process may be monitored by the controller 50.

The controller 50 may also communicate with a display 68 for displaying various programming and operating parameters, a keypad 70 for inputting data, for example, for programming or initiating or stopping of the pumping action, and a communication module 72, for example, communicating wirelessly either through a long-range wireless protocol or short range wireless protocol such as Bluetooth, cellular communication, infrared, WiFi or the like or by a wired protocol such as Ethernet, USB, or other communication protocols. The controller 50 may also communicate with a local barcode scanner 74.

The controller 50 may also communicate with a password memory 73, initially blank to allow entry of a new password, and subsequently holding a password whose entry is required to change the password memory, and for other programming steps as will be described.

Figure 4:
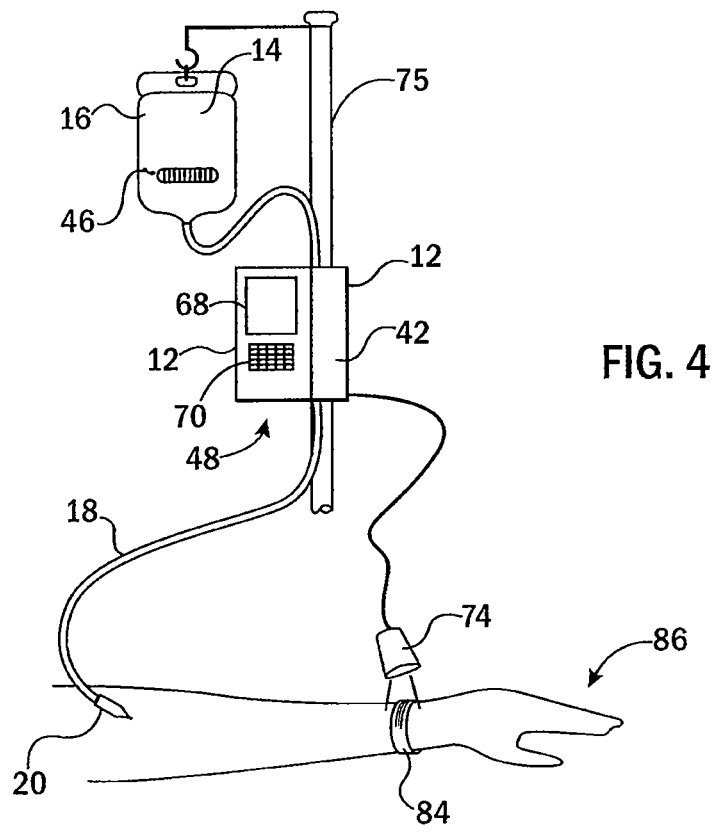
FIG. 4 is a depiction of the pump and drug installed on an IV pole for administration to the patient at a location remote from the site loading of the pump and showing a bar code reader being one method of validating the set up of the remotely loaded pump.

Referring now to FIGS. 1 and 4, the nurse 32 or other specialist may then attach the pump 12 to an IV pole 75 or the like and attach the pouch 16 holding the drug 14 to a point on the IV pole 75 above the pump 12. The barcode 46 will be readily accessible on the pouch 16.

As indicated by process block 81 of FIG. 5, the nurse 32 may then validate the setup by using the barcode scanner 74 to scan a wrist tag 84 on the patient 86 to match the patient identification stored in the pump 12 in the infusion parameter data 58. The barcode scanner 74 may further scan the barcode 46 on the pouch 16 to confirm that it is the correct drug 14. In an alternative embodiment, the function of the barcode scanner 74 may be implemented by a portable wireless device such as an iPhone or Android phone or similar smart device having a camera or similar element that may be used to read the barcode, decode the barcode, and forward the information to the pump 12, for example, by near field communication, Bluetooth, infrared channel or the like. In addition, the barcode scanner 74 may be used to scan the pump 12 itself. In this way, these devices may also be used to positively identify the pump and the drug, as well as the patient, and to allow activation of the pump only if the patient, pump, and drug matches a predetermined link combination stored in the pump 12 or in a remotely accessible database. Clearly, the barcode scanner may be replaced with other local scanning devices including RFID tags and a reader, or the like. The barcode scanner 74 may be implemented as a wireless device and the scanning operation can be performed using a portable device such as a tablet computer, smartphone or the like.

The nurse 32 may then activate the pump as indicated by process block 88 free from the time-consuming loading of drug 14 into the pump 12 and programming of the pump 12 which may now be accomplished by a specialized individual having great familiarity with the systems. Alternatively, the nurse 32 may authenticate the proper setup and patient by reviewing patient biographical information displayed on the screen of the pump 12 including, for example, patient name, date of birth, and the like as stored in the parameters previously described. Confirmation of this information may be indicated by pressing of the keypad button on the pump 12.

In some embodiments, the nurse 32 may program or reprogram some of the pump parameters according to selections made by the originally programming user as will be described below. For example, some pump parameters may be freely programmed by the nurse 32 according to those permissions granted by the original programming user or may be programmed only within a predetermined range established by the original programming user and which may not be changed by the nurse 32.

Figure 6:
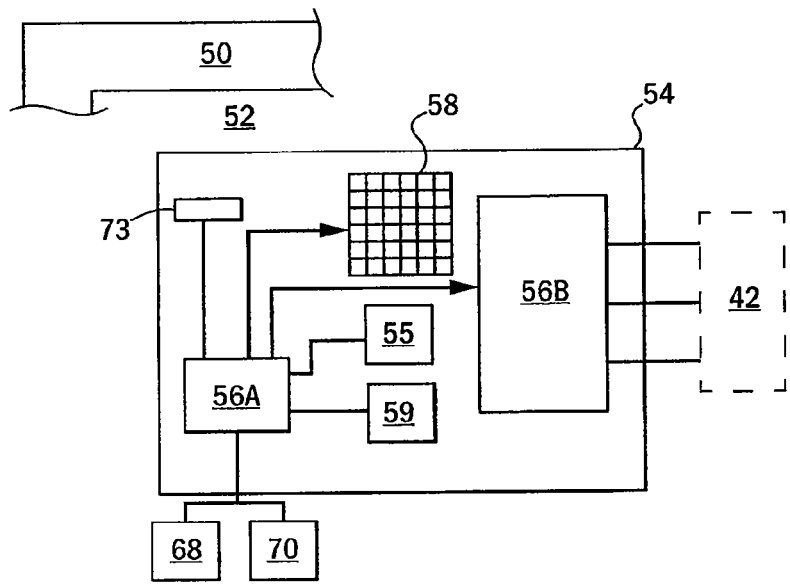
FIG. 6 is a block diagram of data and programming structures of the pump control program of the controller of FIG. 3 including a user interface program controlling the entry of control parameters through the pump user interface.

Referring now to FIGS. 3 and 6, the program 54 of the controller 50 may provide generally an interface program 56a communicating with the display 68 and keypad 70 for sending data to the screen 68 and receiving data from the keypad 70. The interface program 56a may in turn communicate with infusion parameter data 58 allowing programming of infusion parameter data 58 and to display of the infusion parameter data 58 on the display 68. The interface program 56a may also communicate with pump control program 56b serving to provide control signals to the pump section 42, and specifically to output control signals to the pump 64 and receive sensor signals from sensors 61, 62, and 66 as is generally understood in the art.

The interface program 56a may also communicate with a rules table 55 and a lock/hide table 59 as will now be discussed.

Figure 7:
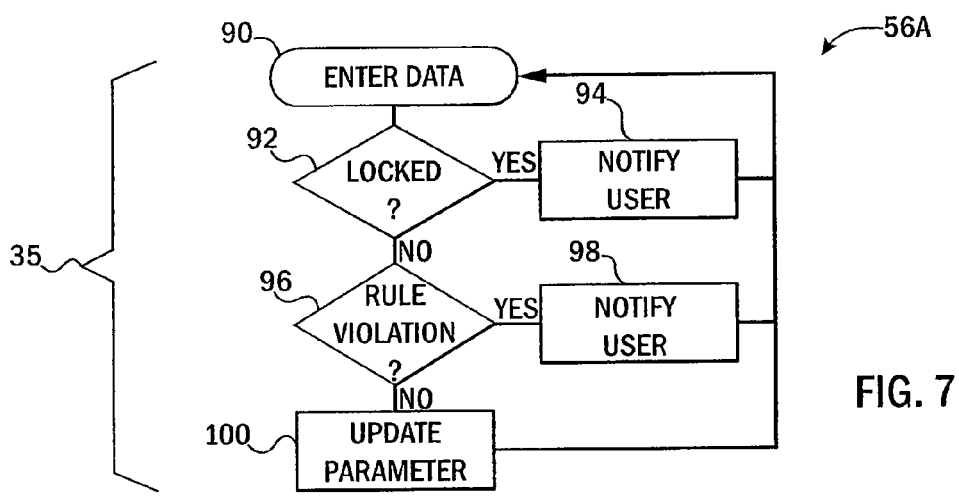
FIG. 7 is a flowchart executed by the user interface program to lock or hide some programmable features.
Figure 8:
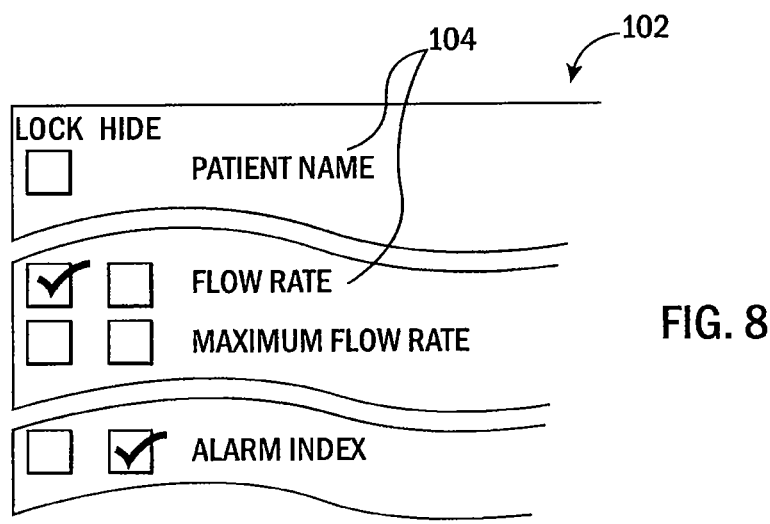
FIG. 8 is a fragmentary representation of a screen display on the pump user interface allowing password-protected locking and hiding of programming features.

Referring now to FIGS. 5, 7 and 8, during programming of the pump 12 by a pharmacist 28 or other specialist per process block 35 of FIG. 5, the interface program 56a may begin a data entry mode indicated by process block 90, for example, as invoked by the pressing of data entry keys on the keypad 70 (per FIG. 3) as is generally understood in the art or through the programming method 40 described above. Upon beginning the data entry mode, the interface program 56a may request the entry of a password by the user. This entry is optional and if no user password is entered, the options for data entry and viewing are limited as will be described below.

The data entry mode will generally display on the display 68 different parameters of the infusion parameter data 58 and allow the entry of data into those parameters in a conventional menu-driven data entry process. At decision block 92, for each parameter selected for entry by the user, the interface program 56a checks the rule table 55 to see if the particular parameter is locked data. If so and if the user is not operating under a predetermined password as described above, the interface program 56a proceeds to process block 94 and the user is notified that this data entry or data change may not be performed and the change in data is rejected. The program then returns to process block 90 for the entry of possibly different data.

If at decision block 92, the parameter is not locked or the user is operating under a password matching the predetermined password, interface program 56a proceeds to decision block 96 and the entered data is received and compared against rules held in rules table 56. Such rules may, for example, (1) provide for predetermined ranges of acceptable data entry for the particular data parameter or (2) compare currently enter data against other previously entered data values for consistency. For example, the rules may identify the drug and based on the drug identification provide a range of possible volume flow rates. The rules or ranges may be entered by a user operating under the password by similar process as described with respect to decision block 92 and 94.

If at decision block 96 a rule is violated, the interface program 56a proceeds to process block 98 and the user is notified of that violation and changed data is rejected. This notification may include an indication of the acceptable range or the reason for the rejection, for example, providing a recitation of the rule.

If at decision block 96 no rule is violated, then at process block 100 the necessary changes in the infusion parameter data 58 are made and additional data may be entered.

Referring now to FIG. 8, population of the lock/hide table 59 may be performed using steps similar to those with respect to decision block 92 and 94 when the interface program 56a is in a data entry mode for the lock/hide table 59. In that mode, the screen of terminal 34 may display a list of programmable data 102 providing a series of parameter names 104 together with checkboxes that allow individual parameters to be either locked or hidden. As discussed above, the state of parameters as locked or unlocked are used at decision block 92 to determine whether the change in that data may be performed by those not operating under the entered password. Hidden data results in the parameters being hidden during the data entry process of process block 35 preventing both programming and confusion by the user. Because the data is hidden, it may not be viewed or modified by those not operating under the entered password.

Generally the parameter data 58 may include: (1) the patient name, (2) the patient birthdate, (3) the patient identification number, (4) the flow/dose rate of the drug to be delivered by the pump, (5) the volume of drug to be infused (VTBI), (6) a maximum allowed flow rate for this patient, (7) an alarm interval for the infusion task (e.g. every 10 milliliters), (8) whether the pump enters a standby state when the alarm is set, (9) occlusion alarm pressure setting, (10) activation state of the air-in-line alarm, and the like. Other alarm settings may include, for example, battery capacity or data from other monitoring devices such as blood pressure, pulse, oximeter value, etc. that may be incorporated into the pump 12.

Generally it will be understood that a mechanism will be provided for resetting the password allowing those users operating under a predetermined password to change the password.

EXAMPLE

A pharmacist may receive a physician's order to dispense a drug to be infused for a patient. The total volume of the drug is 100 mL. The patient is at home and the infusion will be administrated by a visiting nurse, who is not familiar with the pump. According to the lab results and physician's assessment of the patient, the flow rate of the drug for this patient cannot exceed 50 mL/hour and the physician has ordered 25 mL/hour as the infusion flow rate and that the patient pulse and blood pressure should be taken every 10 mL of drug infused.

As part of dispensing the drug, the pharmacist can configure the pump according to the infusion task by invoking a proper programming page on the pump which allows him/her to input the password. After authentication, the pharmacist can input the following information:

Patient information, including name, birth date, and patient identification number;
Flow rate: 25 mL/hour;
Volume to be infused (VTBI): 100 mL;
Maximum allowed flow rate for this patient: 50 mL/hour; and
Alarm interval for this infusion task: every 10 mL of drug infused (the pump can be configured so when the alarm sets off, the pump enters stand-by state).

If preferred, the pharmacist can also configure the pump to hide some user selectable features, such as occlusion alarm pressure setting, air-in-line alarm setting, etc.

After all related information is input and all configurations are completed, the pharmacist can save this infusion task on the pump, and give the pump and the drug to the visiting nurse.

When the visiting nurse arrives at the patient home and turns on the pump, the patient's name is shown on the pump screen for the nurse to confirm. Birth date and patient identification number then can be confirmed. Once necessary information is confirmed as correct, the preloaded pump may be set up and connected to the patient.

Alternatively the pump may guide the nurse to prime the tubing and load the tubing on the pump to connect to the patient and perform other steps otherwise performed by the pharmacist.

Once each step has been confirmed as successfully completed, the flow rate of 25 ml/hour and VTBI of 100 mL are shown on the screen, and the user is prompted to press the "Run" key on the pump keypad to run the infusion. If the pharmacist hides the selectable features to set up occlusion alarm pressure, the nurse will not see the option on the pump. The pump will alarm at the pressure level the pharmacist programmed. After each 10 mL of drug infused, the pump alarms and pauses, prompting the nurse to take pulse and blood pressure measurements. The nurse can press "Run" key again to resume the infusion after the measurements are done. When the nurse tries to increase the flow rate to speed up the process, she cannot go beyond 50 mL/hour, the maximum limit set by the pharmacist as a rule.

The present invention not only simplifies the workflow in administering drugs but allows different pumps to be provided to a given patient for different purposes and allows better utilization of a limited number of pumps. It will be understood that the present invention may work with a variety of different pump types including not only peristaltic pumps but also syringe pumps and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

As used herein programming or data entry refers not only to adding data but modifying or deleting data in electronic memory.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A method of managing patient drug infusions for a patient using a medical pump of a type having a housing;
   a pump supported by the housing to receive an IV line therethrough, the IV line attached to a pre-loaded drug container;
   a carrier configured to hold the housing the IV line and the pre-loaded drug container during transport wherein the carrier is sized to fit within and operate with a pneumatic air tube delivery system providing a six inch internal diameter, the carrier being part of a pneumatic cartridge;
   at least one sensor supported by the housing to monitor a flow of material through the IV line when received within the medical pump, and an electronic computer attached to the pump and supported by the housing and having a memory holding a stored program wherein the electronic computer executes the stored program fixed in non-transitory media and communicates with the pump and at least one sensor to allow programming of at least a portion of the pump parameters based upon an order for a drug infusion for the patient, including a drug identification and a patient identification, controlling operation of the medical pump by a first user and to allow selectively restricting change in the programming of pump parameters by the first user from a second user;
   the method comprising the steps of:
   (a) receiving by a first individual, at a first work area, an order for a drug infusion for the patient providing the drug identification, the patient identification, and infusion parameters;
   (b) programming the medical pump with the pump parameters;
   (c) programming the medical pump to restrict subsequent programming of selected pump parameters by a second user wherein the restricting of subsequent programming parameters hides restricted pump parameters from the second user;
   (d) loading the pump into the carrier;
   (e) transporting the programmed medical pump to a second individual and the patient at a second work area remote from the first work area;
   (f) displaying the patient identification on a visual display; and
   (g) activating the medical pump by the second individual according to its previous programming by the first individual wherein the second individual must confirm by a manual input a match between the patient and the patient identification displayed on the visual display and a match between a local drug identification and the programmed drug identification before allowing operation of the selectable pump parameters received by the programming of the first individual while preventing a change in the programming by the second individual.

2. The method of claim 1 where the restricting of subsequent programming parameters requires that the restricted pump parameters lie in a range programmed by the first user and blocked from changing by the second user.

3. The method of claim 1 including the step of requiring validation by the second individual at the second work area of at least some pump parameters before activation of the medical pump.

4. The method of claim 3 wherein the pump parameters include patient identification, drug identification, and drug delivery rate.

5. The method of claim 4 wherein the medical pump is an infusion pump and the drug is contained in an IV bag attached to an IV line and including the step of loading of the medical pump with the drug by threading the IV line through the pump and locking the line into the pump.

6. The method of claim 3 wherein the step of validation inputs at least one of patient identification, drug identification, and pump identification using tags attached to at least one of the patient, drug container and pump, the tags selected from the group consisting of bar codes and RFID tags.

7. The method of claim 1 wherein the medical pump, drug container and carrier have a weight of less than 12 pounds.

8. The method of claim 1 wherein the medical pump provides a password locking of the programming and including the step of locking the programming performed at step (c) before step (d).

9. The method of claim 8 wherein the medical pump provides a password locking of rules describing a relationship between values of the programming and constraining a reprogramming of the pump by the second individual at the second work area.

10. The method of claim 1 wherein the medical pump includes a communication module and wherein the programming is performed using separate computing device communicating with the medical pump through the communication module through at least one of a wired or wireless connection.

11. A programmable medical pump comprising:
 a housing;
 a pump supported by the housing to receive an IV line therethrough, the IV line attached to a pre-loaded drug container;
 a carrier configured to hold the housing, the IV line and the pre-loaded drug container during transport wherein the carrier is sized to fit within and operate with a pneumatic air tube delivery system providing a six inch internal diameter, the carrier being part of a pneumatic cartridge;
 at least one sensor supported by the housing to monitor a flow of material through the IV line when received within the pump;
 an electronic computer attached to the pump and supported by the housing and having a memory holding a stored program wherein the electronic computer executes the stored program fixed in non-transitory media and communicates with the pump and at least one sensor to:
 (a) receive from a first individual selectable pump parameters including a drug identity and a patient identification, for fully programming an operation of the medical pump;
 (b) receive from the first individual permissions restricting subsequent change in the programming of the selectable pump parameters by a second individual wherein the permissions hide restricted pump parameters from the second individual;
 (c) display the patient identification on a visual display;
 (d) receive from the second individual manual input commands confirming match between a local patient and the patient identification displayed on the visual display and commands confirming a match between a local drug mid the programmed drug identity before allowing operation of the selectable pump parameters received by the programming of the first individual while preventing a change in the programming by the second individual; and
 (e) receive an activation command from the second individual activating the pump to operate according to the selectable pump parameters wherein the memory stores parameter data including a dose, a volume flow rate, the drug identity, and the patient identification.

12. The programmable medical pump of claim 11 where the permissions require that the restricted pump parameters lie in a range programmed by the first individual and blocked from changing by the second individual.

13. The programmable medical pump of claim 11 wherein the electronic computer communicates with a programmable data table providing a listing of a portion of pump parameters controlling operation of the pump, and wherein the electronic computer further executes the stored program to allow programming of the portion of the pump parameters only if a password received from the first individual matches a predetermined password.

14. The programmable medical pump of claim 13 wherein the electronic computer further executes the stored program to allow operation of the pump only if entered data parameters are consistent with a. set of stored rules describing relationship between parameters.

15. The programmable medical pump of claim 11 wherein the electronic computer communicates with a programmable data table providing a listing of a portion of pump parameters controlling operation of the pump, and wherein the electronic computer further executes the stored program to allow viewing of the portion of pump parameters only if the password received by the first individual matches a predetermined password.

16. The programmable medical pump of claim 15 wherein the electronic computer further executes the stored program to allow programming of the programmable data table only if the password received from the individual matches the predetermined password.

17. The programmable medical pump of claim 14 wherein the electronic computer communicates with a programmable data table holding the stored rules, and wherein the electronic computer further executes the stored program to allow changing of the rules of the programmable data table only if the password received from the individual matches the predetermined password.

18. The programmable medical pump of claim 11 wherein the medical pump includes a communication module for programming and operation of the medical pump using a separate computing device communicating with the medical pump through the communication module through at least one of a wired or wireless connection.

19. A medical pump system comprising:
 a housing;
 a medical pump supported by the housing and providing a portion for receive an IV line to pump fluid through the IV line while monitoring fluid pumping under computer control, the IV line attached to a pre-loaded IV bag;
 a carrier receiving the medical pump when loaded with the IV bag and an IV tube for use, the carrier stably supporting the medical pump, IV bag and IV tube for enclosure fitting within and operation with a pneumatic air tube delivery system providing a six inch diameter cylinder, the carrier being part of a pneumatic cartridge;

at least one sensor supported by the medical pump to monitor a flow of material through the IV line when received within the medical pump;

an electronic computer attached to the medical pump and having a memory holding a stored program wherein the electronic computer executes the stored program fixed in non-transitory media and communicates with the medical pump and at least one sensor to:

(a) receive from a first individual selectable pump parameters based upon an order for a drug infusion for a patient, including a drug identity and a patient identification, for fully programming an operation of the medical pump;

(b) receive from the first individual permissions restricting subsequent change in the programming of the selectable pump parameters by a second individual;

(c) display the patient identification on a visual display;

(d) receive from the second individual manual input commands confirming a match between a local patient and the patient identification displayed on the visual display and commands confirming a match between a local drag and the programmed drug identity before allowing operation of the selectable pump parameters received by the programming from the first individual while preventing a change in the programming of the second individual; and (e) receive an activation command from the second individual activating the medical pump to operate according to the selectable pump parameters wherein the memory stores parameter data including a dose, a volume flow rate, the drug identity; and the patient identification.

* * * * *